United States Patent [19]

West

[11] Patent Number: 5,312,558
[45] Date of Patent: May 17, 1994

[54] PESTICIDE COMPOSITION

[75] Inventor: Michael H. West, Sanatobia, Miss.

[73] Assignee: IBC Manufacturing Company, Memphis, Tenn.

[21] Appl. No.: 680,434

[22] Filed: Apr. 4, 1991

[51] Int. Cl.$^5$ ............................................. C11D 3/48
[52] U.S. Cl. ................................. 252/106; 106/18.31; 106/18.32; 252/544; 252/545; 514/115
[58] Field of Search ............... 252/544, 545, DIG. 17, 252/106

[56] References Cited

U.S. PATENT DOCUMENTS 5,039,441  8/1991  Thomas et al. ...................... 252/142
5,059,335 10/1991  Rizvi et al. .......................... 252/32.5

FOREIGN PATENT DOCUMENTS 0013450  7/1980  European Pat. Off. .
0103450  7/1980  European Pat. Off. .
0199383 10/1986  European Pat. Off. .
0314232  5/1989  European Pat. Off. .
0417987  3/1991  European Pat. Off. .
  86457 12/1971  German Democratic Rep. .

Primary Examiner—Richard D. Lovering
Assistant Examiner—Joseph D. Anthony
Attorney, Agent, or Firm—Fred Philpitt

[57] ABSTRACT

A pesticide composition comprising a pesticide, an emulsifier and a formulation formed by combining a water dispersible solvent, an orthophosphonis acid, cocodimethyl amine and optionally a phosphonic acid.

2 Claims, No Drawings

PESTICIDE COMPOSITION

This invention pertains to compositions which are
(1) suitable for dispersing pesticides in water, or
(2) suitable for bleaching organic stains from hard surfaces, or
(3) suitable as corrosion inhibitors.

My compositions may comprise, consist of, or consist essentially of the salts or partial salts of
(a) an alkyl amine or dialkyl amine and
(b) an orthophosphoric acid
together with a compatible solvent for such salts or partial salts.

It is known that industrial biocides perform better if they are well dispersed in the water in which they are used or applied. It is also known that smaller particles of pesticides give better coverage and better prevent the entrance of pests into treated articles. It is desirable for many uses to produce a true solution of the pesticide which gives molecular size distribution.

I have found that it is possible to produce molecular dispersions in water dilutions of man water-insoluble pesticides by formulating them with the dispersant compositions of the present invention. I have also found that these molecular dispersions provide unexpectedly good levels of pesticidal activity and that the solutions are non-corrosive to mild steel.

I contemplate a composition formed by combining the following ingredients:

| solvent (water dispersible) | 10–50 parts by wt |
| an Orthophosphoric Acid | 10–40 parts by wt |
| an alkyl or dialkyl amine | 20–60 parts by wt |
| an emulsifier | 0–25 parts by wt |

Water-dispersible solvents which I have found suitable for producing compositions in accordance with this invention comprise, but are not limited to, alcohols, glycols, and glycol ethers. The water-dispersible solvent may also consist partly or totally of water itself.

Alkyl and dialkyl amines that I have found useful for compositions of this invention comprise, but are not limited to, dodecyl dimethylamine, didecyl methyl amine, dodecyl amine, decyl dimethyl amine, cocodimethyl amine, N, N-dimethylcocoamine, cocoalkyldimethylamines and dicoco methyl amine.

Emulsifiers or surfactants that I have found useful for compositions of this invention comprise, but are not limited to, cocodimethyl ammonium chloride, didecyl dimethyl ammonium chloride, alkyl benzyl dimethyl ammonium chlorides, and alkylphenol ethylene oxide adducts. Emulsifiers or surfactants make a better product, but since they are not absolutely essential, I consider that they are optional ingredients.

When my composition is used to disperse a pesticide the ingredients and their amounts are preferably as follows:

| Chemical Ingredient | Range of Amounts Parts by Weight |
|---|---|
| Solvent | 10–40 |
| Emulsifier | 0–20 |
| Orthophosphoric acid (85% in water) | 5–15 |
| Pesticide | 3–9 |
| Amine | 30–60 |

The range of dilutions in parts of ingredients per part of water or solvent may be from about 1-10 to about 1-300.

A specific example of such a composition would be

| Chemical Ingredient | Parts by Weight |
|---|---|
| Propylene Glycol, methylether (solvent) | 26 |
| Poly(oxy-1,2-Ethandiyl), Alpha (Nonyl-phenyl)-Omega-Hydroxy (emulsifier) | 15 |
| Orthophosphoric acid (85% in water) | 8 |
| 3-Iodo-2-Propynyl Butyl Carbamate (pesticide) | 6 |
| Cocodimethylamine | 45 |

The carbamate pesticide and may be replaced by other pesticides.

As another embodiment of my invention I contemplate that the above compositions may also contain 1-15 parts by weight of a phosphonic acid. In this regard commercial liquid phosphonic acids which I have found useful comprise, but are not limited to the following:

Phosphonic acid, {nitrolotris (methylene)}tris
Phosphonic acid, {{{bis{2-bis(phosphonomethyl)amino]ethyl]amino}-methyle
Phosphonic acid, (1-hydroxyethylidene)bis-
Polyhexylene polyamino polymethylene phosphonic acid A specific example of a composition containing both an amine, an orthophonic acid and a phosphonic acid would be as follows:

| Chemical Ingredient | Parts by Weight |
|---|---|
| Propylene Glycol, methylether (solvent) | 30 |
| Poly(oxy-1,2-Ethanidiyl),(Alpha(Nonyl-phenyl)- Omega-Hydroxy (Emulsifier) | 5 |
| Orthophosphoric Acid (85% in water) | 5 |
| Coco Dimethylamine | 50 |
| Phosphonic acid (1-hydroxyethylidene)bis (60% in water) | 10 |

This composition can be used for bleaching organic stains on firm surfaces, or as a corrosion inhibitor, or as a dispersant for insecticides.

Pesticides which I have found useful when dispersed by compositions of the present invention comprise, but are not limited to, commercial compositions of polyphase, azaconazole, 2,5-dichloro 2-n-octyl-3-isothiazoline, and Tebuconazole. Useful ranges of pesticides formulated with compositions of my invention are from about 1 to about 20 parts by weight per 100 parts by weight of the composition.

Dispersant compositions of the present invention formulated with pesticides were used for treating wood, textiles, paper, tile, brick, concrete and leather. Treating dilutions in water of from 0.1% to 10% according to the generalized formula gave control of biological growths on the treated articles which were as good or better than that offered by commercially accepted products at similar use dilutions. Compositions of the present invention with the above mentioned pesticides were also tested to determine control of algal, fungal, and bacterial slimes in water. At treating levels from 0.1% to 1%, all slimes were controlled. All of the compositions were tested at 1% in water and found to be non-corrosive to mild steel.

My dispersant composition may be combined with a pesticide in a number of different ways. For instance, the dispersant composition can be mixed with water (e.g. 100 parts of water per one part of dispersant composition) and then combined with 0.1–1.0 part of the pesticide formulation. The combination then may be further diluted with water, the degree of dilution depending upon the particular situation to be treated. This is largely a matter of routine testing that those working in this art can readily carry out in order to obtain optimum results.

The following composition is useful for bleaching organic stains such as iron tannates from hard surfaces such as wood and vinyl:

| Ingredients | Parts by Weight |
| --- | --- |
| Cocodimethylamine | 4.5 |
| Phosphoric acid (1-hydroxyethylidene) bis (60% in water) | 1.5 |
| Water | 94.0 |

It will be apparent those skilled in the art that many different formulation combinations must be tested to find one with optimum physical and efficacy properties. With the information given in this disclosure the skilled chemist will be able to both develop formulations of dispersant compositions and compatible pesticides with optimum physical and biological properties for a particular application, as well as bleaching compositions for removing organic stains from hard surfaces.

I claim:

1. A pesticide composition in the form of a molecular dispersion comprising:

| | | |
| --- | --- | --- |
| (a) a solvent (water dispersible) | 10–40 | parts by wt. |
| (b) an orthophosphoric acid (85% in water) | 5–15 | parts by wt. |
| (c) cocodimethyl amine | 30–60 | parts by wt. |
| (d) a water-insoluble pesticide | 3–9 | parts by wt. |
| (e) an emulsifier | 0–20 | parts by wt. |

2. A composition according to claim 1 which further comprises: (f) a phosphonic acid 1–15 parts by wt..

* * * * *